United States Patent [19]

Youdin et al.

[11] 4,207,959

[45] Jun. 17, 1980

[54] WHEELCHAIR MOUNTED CONTROL APPARATUS

[75] Inventors: Myron Youdin, Flushing; Mario W. Clagnaz, Jr., Floral Park; Henry Louie, Brooklyn, all of N.Y.

[73] Assignee: New York University, New York, N.Y.

[21] Appl. No.: 911,771

[22] Filed: Jun. 2, 1978

[51] Int. Cl.² .............................................. B62D 1/24
[52] U.S. Cl. ..................................... 180/167; 46/256; 180/6.5; 180/DIG. 3
[58] Field of Search ..................... 180/6.5, 98, DIG. 3, 180/167; 46/256, 210

[56] References Cited

U.S. PATENT DOCUMENTS

| 2,974,441 | 3/1961 | Denner | 46/256 |
| 2,995,866 | 8/1961 | Johnson | 46/256 |
| 3,961,441 | 6/1976 | Sato | 46/256 |

*Primary Examiner*—John A. Pekar
*Attorney, Agent, or Firm*—Darby & Darby

[57] ABSTRACT

A voice actuated wheelchair control apparatus is disclosed which allows a quadriplegic to control the speed and direction of travel of a motorized wheelchair by spoken commands. The apparatus includes means for executing spoken commands for initiating incremental changes in the chair's speed or direction of travel. The apparatus also includes means for executing spoken commands which modify or override the wheelchair motion initiated by previously spoken commands.

14 Claims, 9 Drawing Figures

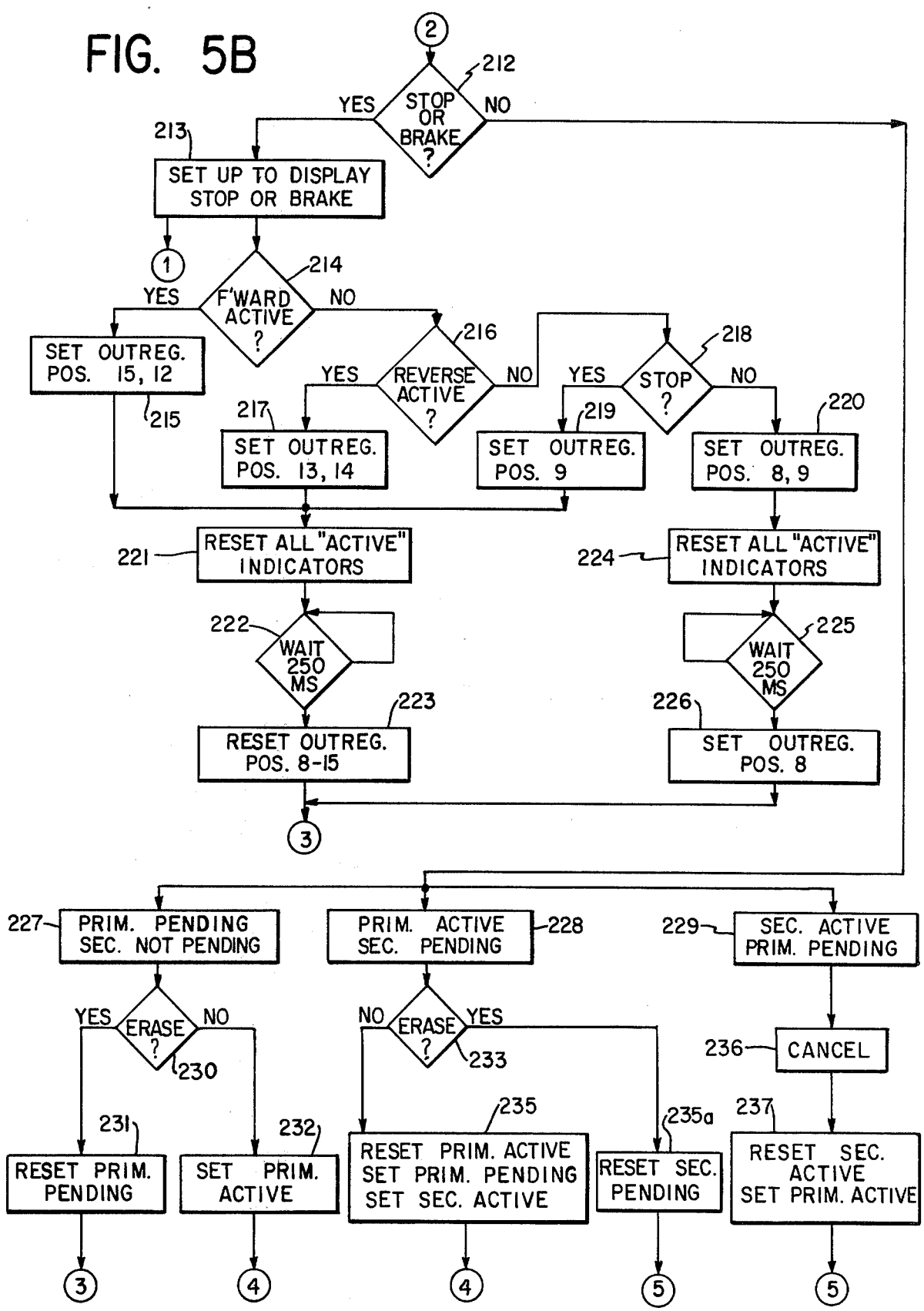

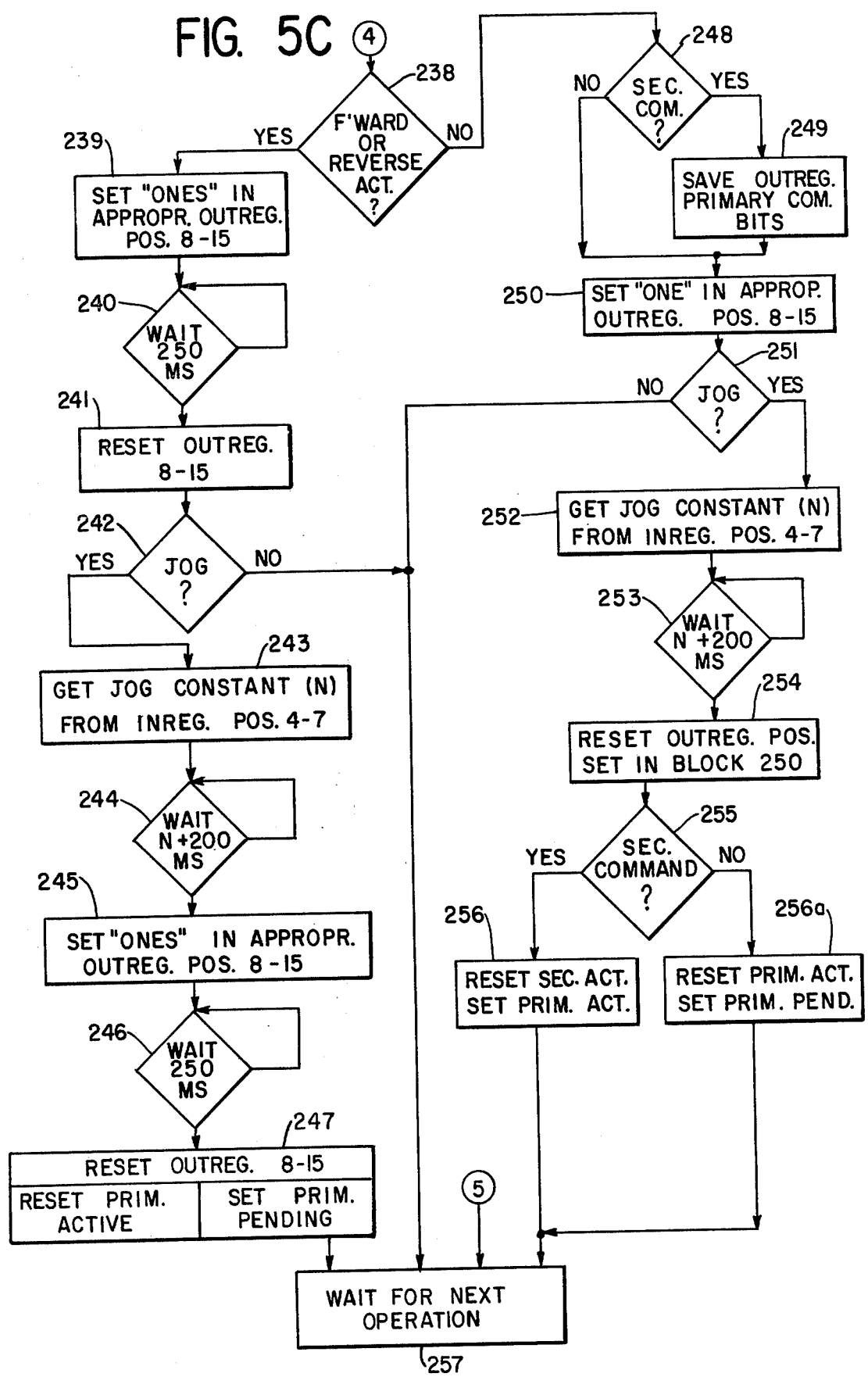

WHEELCHAIR MOUNTED CONTROL APPARATUS

BACKGROUND OF THE INVENTION

1. Field of the Invention

This invention relates to motorized wheelchairs and, more particularly, to wheelchair mounted control apparatus for enabling disabled persons to control the operation of a motorized wheelchairs by means of voice commands.

2. Description of the Prior Art

Particularly for persons paralyzed from the neck down the problem of operating or controlling a motorized wheelchair has been formidable. Conventional powered wheelchair control systems employ a "joy stick" or other control means which must be operated by the hands of the invalid.

Various methods have been proposed for allowing a quadriplegic to control a motorized wheelchair. For example, systems have been proposed which allow the quadriplegic to control a wheelchair by means of head or eye movements. Eye movement systems suffer the disadvantage of being sensitive to the intensity of ambient light. Head movement systems, on the other hand, require somewhat unnatural movements of the head in order to control the chair. These movements may be psychologically undesirable for an invalid who desires to appear as "natural" as possible to the outside world. Both of the above systems provide only limited control capability. For example, neither system provides the capability to make small adjustments in the direction of travel of the chair which are necessary to correct the "drift" which occurs when the chair travels over irregular terrain.

Breath-controlled wheelchair systems are also known in the art. In these systems the invalid controls the chair by sucking or blowing into one or more tubes. The degree of control which can be provided is limited by the number of tubes used. Thus, a high degree of control would require a large number of tubes, and such a system would be too complex for effective operation by the invalid.

A voice controlled wheelchair described by Clark, et al (Arch. Phys. Med. Rehabil., Vol. 58, pp. 169-75, 1977) includes provisions for slowly accelerating the chair to the left or to the right while the chair is traveling in a forward direction. No provision is made, however, for causing small positioning movements of the chair while it is at rest or traveling in a reverse direction. This limits the ability of the operator to make small positioning movements of the chair in restricted areas.

It is an object of the present invention therefore to provide a powered wheelchair control apparatus which allows a quadiplegic to exercise a high degree of control over the wheelchair.

It is a further object of the present invention that the invalid is not required to make any unnatural movements of the body in order to control the wheelchair.

It is yet a further object of the invention to provide apparatus for enabling the wheelchair operator to make changes in the speed or direction of travel of the wheelchair while the chair is or is not in motion.

It is a still further object of the invention to provide apparatus for accomplishing such changes in the speed or direction of travel of the chair in small incremental steps.

It is a still further object of the invention to provide apparatus to prevent the performance of those changes in the direction of travel of the wheelchair which could prove hazardous to the operator.

GENERAL DESCRIPTION

In accordance with a preferred but nonetheless illustrative embodiment of the invention a wheelchair-mounted control apparatus is provided which includes a voice processor which has the capability of converting a preselected set of words spoken by the wheelchair's operator into a corresponding set of computer recognizable signals. Such processors are commerically available and their details are not part of the present invention. In the present embodiment this set of words comprises the commands necessary to control the wheelchair's motion. The apparatus also includes a microcomputer programmed to respond to the appropriate signals which it receives from the voice processor, to selectively activate a set of control lines which, in turn, cause a wheelchair controller to control the wheelchair in the manner specified by the commands spoken by the operator.

The apparatus provides means for recognizing whether a given command or sequence of commands is "primary" or "secondary". A primary command or command sequence is used to initially cause the desired wheelchair motion. A secondary command or command sequence may be used to produce a temporary correction or adjustment to the motion initiated by the previous primary command or command sequence.

Six primary commands are preferably used, namely FORWARD, REVERSE, LEFT, RIGHT, FASTER and SLOWER; these commands being defined as function commands. In the present embodiment the recognition of any of these function commands causes the appropriate indicator (such as a light) on a display panel to be actuated. No action takes place until the operator verifies that the desired command has been recognized by an additional command, such as "GO" or "JOG". The GO and JOG commands are defined as activation commands. Thus, wheelchair motion may only be initiated as a result of a command sequence comprising a function command and activation command.

Issuance of the GO command causes the wheelchair to be propelled in the manner specified by the previous function command until the operator gives a further command, as by saying either "STOP" or "BRAKE", which are commands which are always executed immediately. Issuance of the JOG command causes the wheelchair to be propelled in the manner specified by the previous function command for only a preset short time duration. In the present embodiment this JOG duration time is controlled by a JOG duration switch which is a thumbwheel switch having ten positions. Position "0" of the switch corresponds to a JOG duration of 200 milliseconds; the JOG duration increases as the thumbwheel switch is set to further positions until it reaches a maximum duration of 2 seconds when set to switch position "9".

It will be noted that alternative embodiments are possible employing a plurality of JOG commands such as a JOG 1 command, a JOG 2 command and a JOG 3 command. In such an embodiment each JOG command would correspond to a unique multiplier, e.g., "1" for a JOG 1 command, "2∞ for JOG 2 command and "4" for a JOG 3 command. The JOG duration would then be equal to the duration selected by the JOG duration switch times the multiplier corresponding to the particular command issued. In the example given above, for instance, if the JOG duration switch were set to position "0" the JOG duration obtained by the issuance of the JOG 1, JOG 2 and JOG 3 commands would be 200 miliseconds, 400 milliseconds and 800 milliseconds respectively.

The operator may issue the JOG command a multiple number of times without having to repeat the desired function command each time. He may also follow a sequence of JOG commands by a GO command. The primary function command may be cleared at any time by issuing either a BRAKE command or a STOP command.

By issuing a secondary command sequence the operator may change the speed or direction of travel of the wheelchair without first stopping the chair each time he wishes to make such a change. The secondary function, which is the wheelchair operation initiated by a secondary command sequence acts to modify (FASTER or SLOWER) or override (LEFT or RIGHT) the active primary function or wheelchair operation initiated by the previous primary command sequence. Upon recognition of a secondary command while the wheelchair is being driven in accordance with a previous active primary command sequence, the apparatus causes the appropriate function indicator on the display panel to be actuated to verify that the correct word has been recognized. A subsequent GO command activates the secondary function and causes the previous primary function to become "pending". The apparatus causes the wheelchair to be propelled in accordance with the secondary function until the operator issues a CANCEL command. At this time the primary function again becomes active. The operator may then activate another secondary function if he so desires.

As in the case of primary commands, all wheelchair operations can be stopped at any time by use of the STOP command or BRAKE command. The STOP and BRAKE commands return the apparatus to an idle state in which it is ready to accept the next primary command or command sequence. The BRAKE command will also cause the apparatus to apply the wheelchair brakes if the wheelchair is so equipped.

A secondary function may also be activated by the use of the JOG command. In this case the apparatus will cause the wheelchair to be propelled in accordance with the secondary function for the JOG duration period. The primary function resumes automatically at the end of the JOG duration. This feature of the invention enables the operator to make minor course corrections while en route. For example, the chair may be caused to JOG LEFT or JOG RIGHT while it is moving in the forward direction. These course corrections may be necessary, for example, when the chair is travelling over irregular terrain.

It is another feature of the apparatus of the present invention that activation of secondary functions which could prove hazardous to the user is prevented. For example, a secondary function of LEFT is not permitted if the primary function is RIGHT. Likewise, a secondary REVERSE cannot follow a primary FORWARD.

An ERASE command may be issued following a function command which has not yet been issued. It acts to return the apparatus to the state it was in prior to the issuance of the function command. The ERASE command is useful in situations wherein the operator changes his mind as to the function to be performed before he issues the function command of a command sequence.

The foregoing brief description, as well as further objects, features and advantages of the present invention will be more fully understood by reference to the following detailed description of the presently preferred (but nonetheless illustrative) embodiment in accordance with the present invention when taken in conjuction with the accompanying drawings wherein.

Figure 5A:
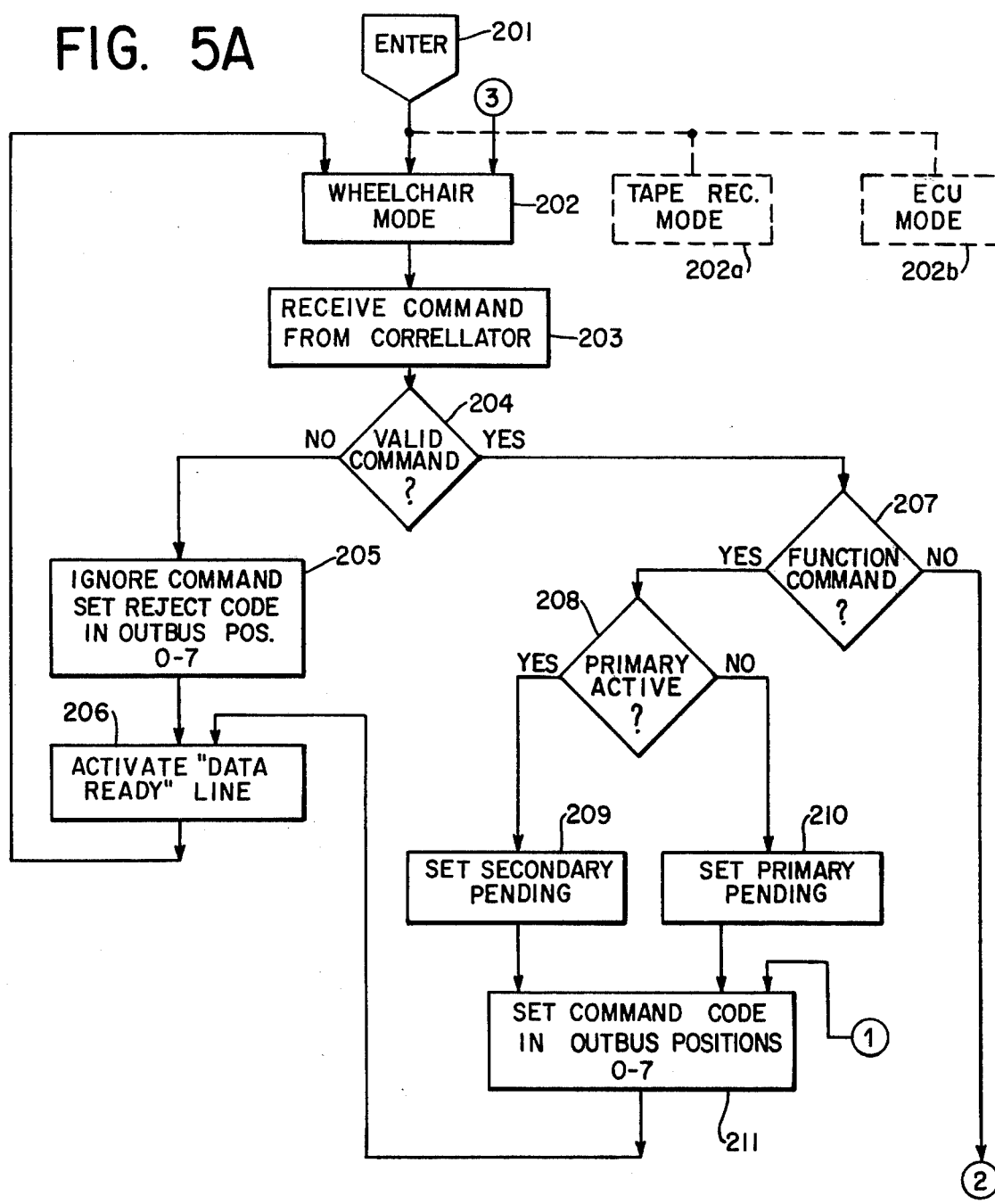
Figure 6:
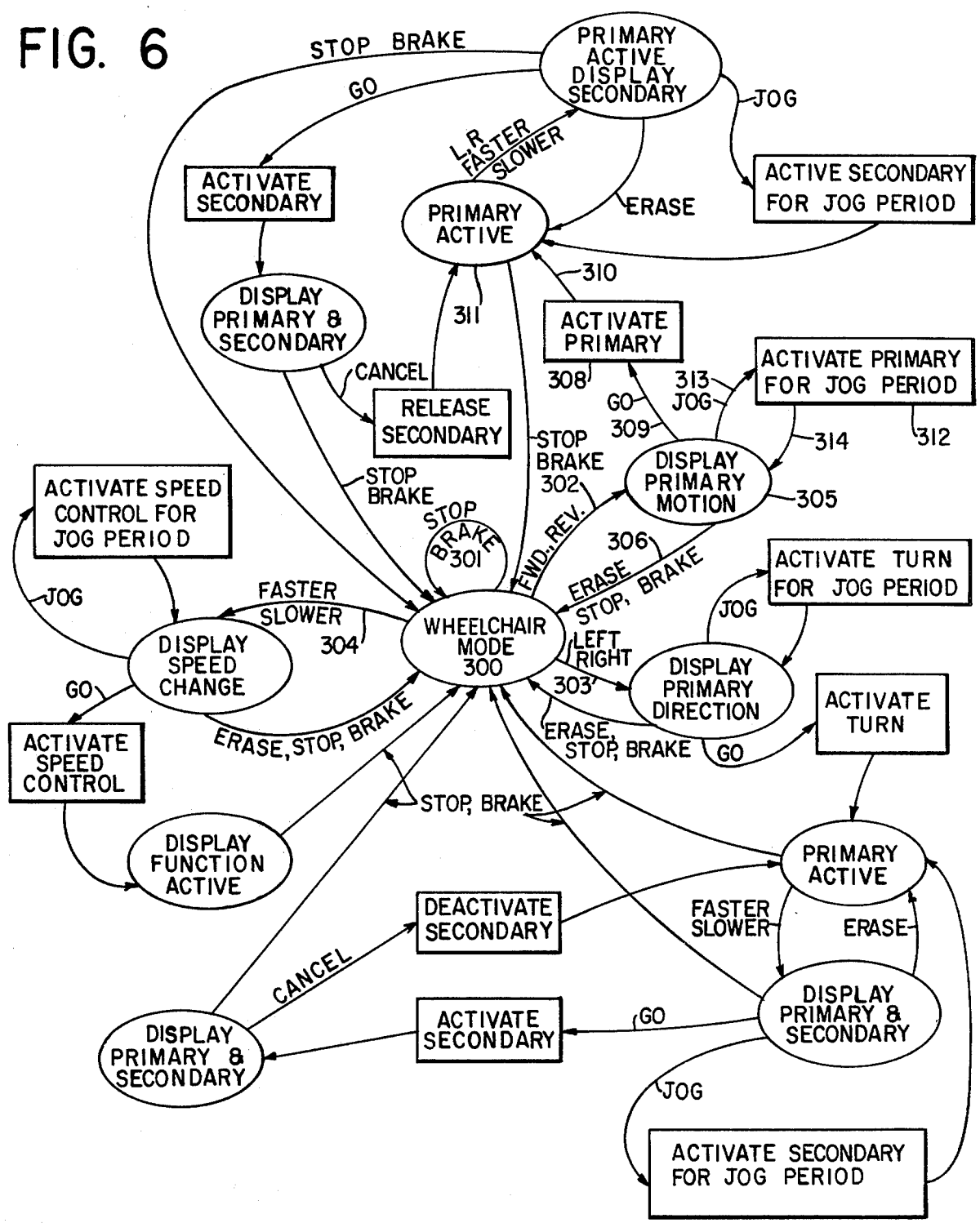
Figure 7:
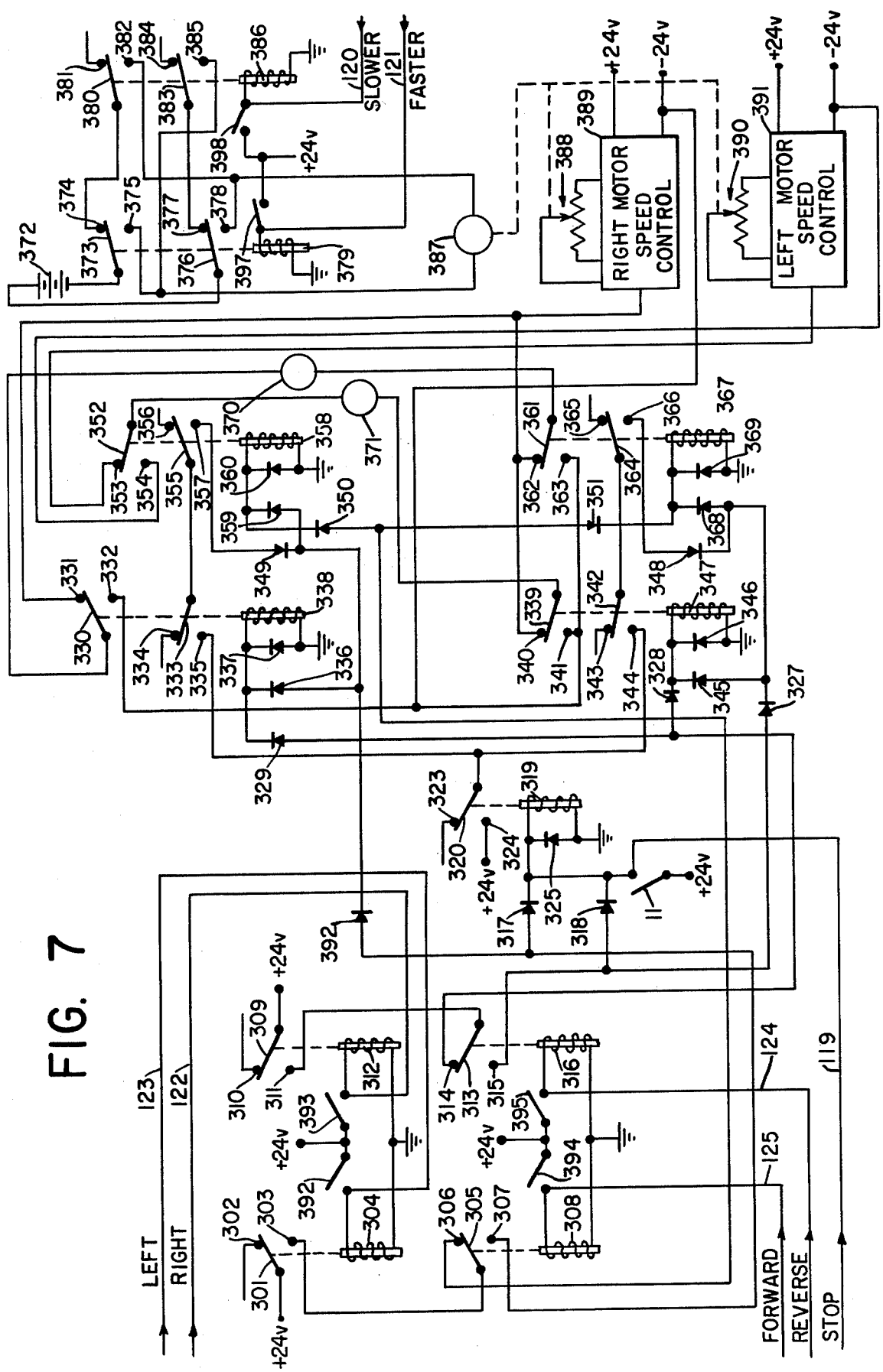

FIGS. 5A, 5B and 5C comprise a simplified flow chart of a programming means in accordance with the present invention;

FIG. 6 is a state diagram illustrating the valid sequences of wheelchair commands which may be issued by the wheelchair's operator;

FIG. 7 is a circuit diagram of a wheelchair controller in accordance with the present invention.

DESCRIPTION OF THE PREFERRED EMBODIMENT

Figure 1:
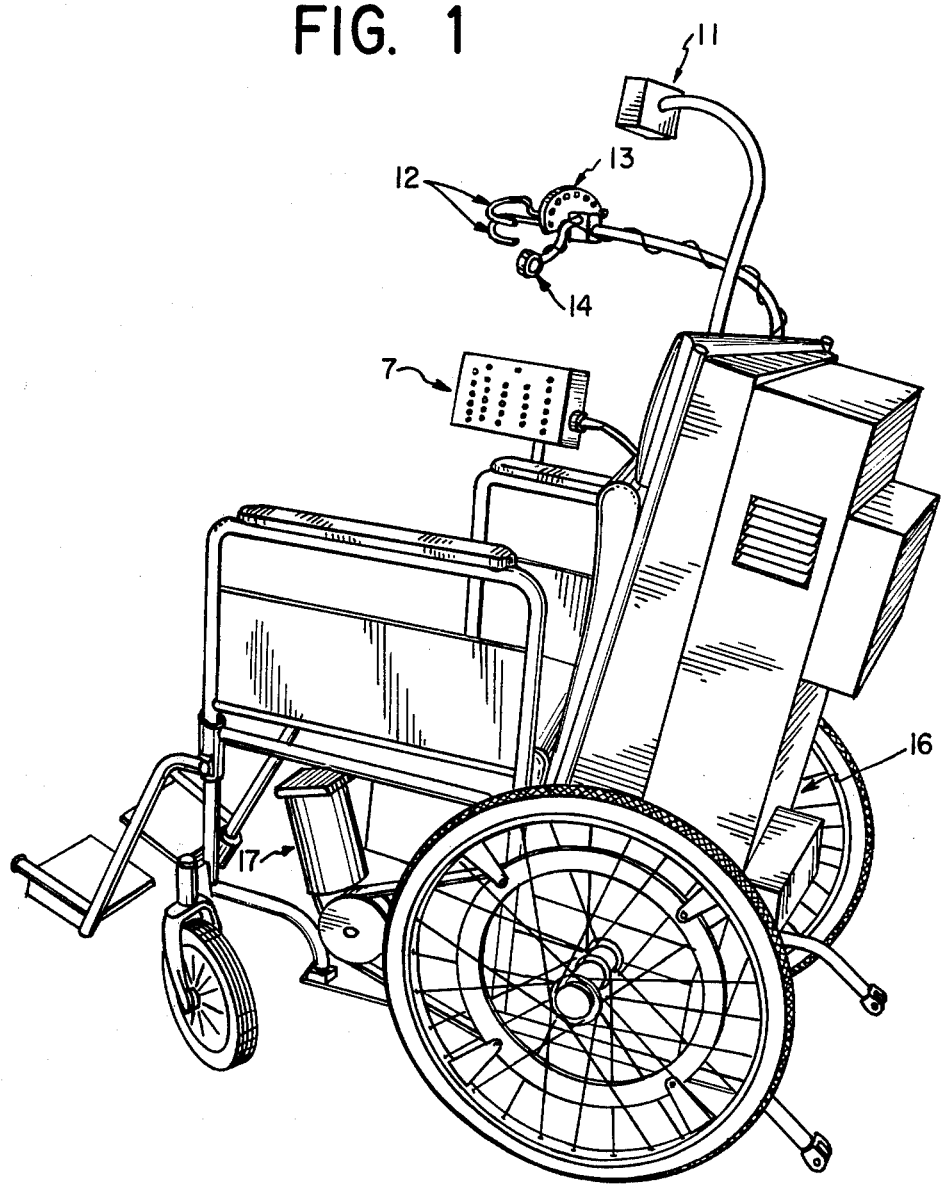
FIG. 1 is a pictorial representation of a powered wheelchair equipped with the apparatus of the present invention.

Referring to FIG. 1, there is shown a pictorial diagram of a powered wheelchair equipped with an apparatus in accordance with the invention. The wheelchair is equipped with a microphone 14 adapted so that it may be positioned sufficiently close to the patient's mouth so tht extraneous noise does not interfere with the wheelchair commands spoken by the patient. Display panel 17 provides the patient with a visual indication of the status of the operations being performed by the apparatus.

It is a feature of the invention that the speed at which the wheelchair will travel may be pre-set by voice command before any actual motion of the wheelchair takes place. Speed indicator 13 gives a visual indication to the patient of this pre-set speed setting. In the present embodiment, the speed indicator is comprised of eight light-emitting diode (LED) circuits, the highest speed being indicated when all eight LEDs are lit, and the lowest speed being indicated by the absence of illumination of any LEDs. It will be appreciated, however, that other speed indicators such as a standard electrical meter may be used.

The wheelchair is also provided with an emergency stop switch 11, of an alternating action type, adapted to be positioned sufficiently close to the patient's head so that a small movement of his head will cause the switch to be activated and thereby deactivate the wheelchair's controls and bring the wheelchair to an immediate stop. The controls remain deactivated until a second actuation of emergency switch 11.

The chair is also provided with breath control tubes 12 which are adapted to be used in connection with a "puff and sip" wheelchair control system such as the one described in the paper of Youdin, et al, Proceedings of the Fourth Annual Conference on Systems and Devices for the Disabled, June, 1977, pp. 147-50. The present embodiment of the voice-controlled wheelchair control apparatus is adapted to override the voice-activated controls with controls activated by the puff and sip tubes. This facility would be used in the event of a malfunction in the voice operated controls.

Figure 2:
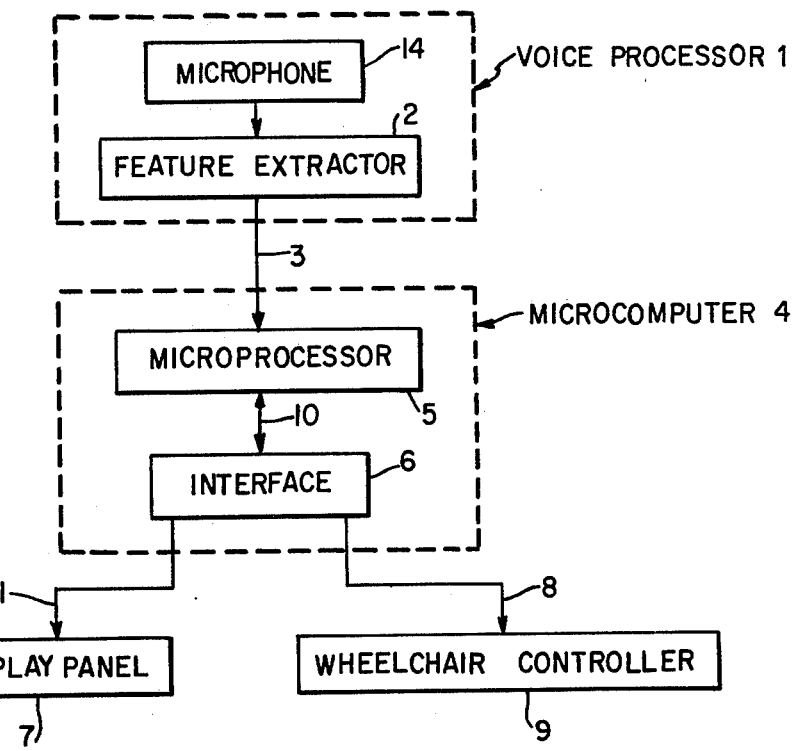
FIG. 2 is an overall block diagram of an apparatus in accordance with the present invention.

Referring to FIG. 2 there is shown a simplified block diagram of a control apparatus in accordance with the invention. The apparatus includes voice processor 1, which in the present illustrative embodiment is a commerically available unit such as the one manufactured by Threshold Technology Inc. Voice processor 1 includes microphone 14 which is connected to feature extractor 2. Feature extractor 2 breaks down spoken words picked up by microphone 14 into a number of distinct audio features and converts the resulting characteristics of the words into a set of computer-recognizable electrical signals 3 which are fed to microcomputer 4. Microcomputer 4, includes microprocessor 5 which may also be commercially available. Microprocessor 5 contains a program for correlating the characteristics of the input words with the characteristics of a preselected vocabulary of words which are selected to be the desired valid wheelchair commands. Microprocessor 5 in combination with other appropriate programming means, in known manner is arranged to act through system bus 10 and interface 6 to activate the appropriate ones of indicator drive lines 11 to cause the appropriate indicators of display panel 7 to be lit, and to activate the appropriate ones of control lines 8 to cause controller 9 to propel the wheelchair in the manner specified by the input command.

Figure 3:
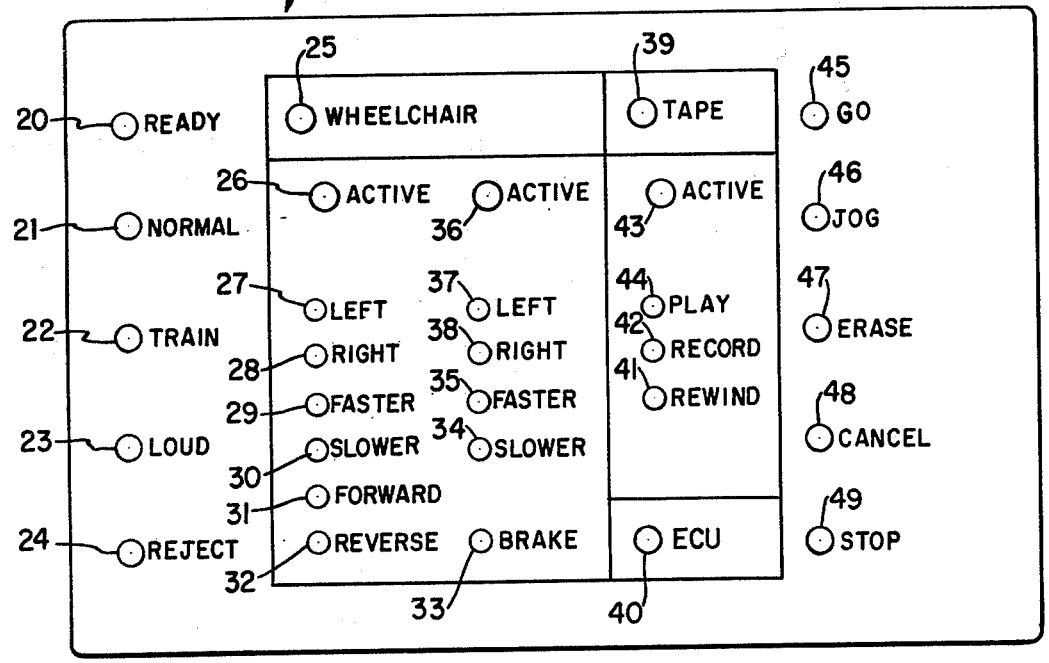
FIG. 3 is a pictorial diagram of the display panel of the apparatus.

FIG. 3 is a more detailed pictorial representation of display panel 7. Indicators 20, 21, 22 and 23 are used in the operation of defining the vocabulary of words that will be recognized as valid wheelchair commands. This operation is not a part of the subject matter of the present invention. Likewise, indicators 39, 43, 44, 42, 41 and 40 are used in the operation of a voice-controlled tape recorder or a voice-controlled environmental control unit which are not a part of the subject matter of the present invention.

Reject indicator 24 is lit when a word spoken by the operator is not recognized as a valid command by voice processor 1 and microprocessor 5, or when an otherwise valid command is issued in an incorrect sequence, taking into account the previous sequence of commands. It is a feature of the invention that the operator is prevented from inadvertently issuing certain sequences of commands which could result in potentially harmful operation of the wheelchair. An example of such a sequence would be a FORWARD command sequence followed by a REVERSE command without an intervening command to stop the wheelchair. An understanding of the allowable sequences of command may be gained by reference to FIG. 6, which is discussed later in the specification.

When the apparatus is activated to accept commands for the operation of the wheelchair, wheelchair mode indicator 25 is lit. A command of LEFT, RIGHT, FASTER, SLOWER, FORWARD or REVERSE, causes the appropriate one of indicators 27, 28, 29, 30, 31 or 32 to light. A subsequent GO command causes GO indicator 45 and ACTIVE indicator 26 to light. During the period of time that ACTIVE indicator 26 remains lit the wheelchair drive motors are activated to propel the wheelchair in the manner indicated by the appropriate indicator light, e.g., when "FORWARD" indicator 31 is lit the wheelchair drive motors are activated to propel the chair in a forward direction.

If the primary function is activated with a JOG command, rather than a GO command, JOG indicator 46 and ACTIVE indicator 26 are lit for the jog duration time. The wheelchair motors, in this case, are activated to propel the wheelchair in the manner specified by the primary function command, but only for the jog duration.

If, instead of issuing either a GO command or a JOG command, the operator issues a CANCEL command, the appropriate one of indicators 26, 27, 28, 29, 30, 31, or 32 is turned off, and the apparatus is conditioned to accept a new command.

As previously mentioned, a feature of the present invention is the ability of the apparatus to accept secondary commands which have the effect of overriding or modifying the actions initiated by primary commands. The secondary commands available to the operator are LEFT, RIGHT, FASTER and SLOWER. To prepare for a secondary operation the operator issues the appropriate function command while primary active indicator 26 is lit indicating that the apparatus is executing a primary function. If the command is a valid one, the appropriate one of indicators 37, 38, 35, 34, or 33 will be lit. A subsequent GO command will cause primary active indicator 26 to be turned off, secondary active indicator 36 to be lit, and the function specified by the secondary function command to be executed by the wheelchair controller 9. The wheelchair controller 9 continues to execute the secondary operation until the issuance of a CANCEL command. Upon the recognition of a CANCEL command, cancel indicator 48 is lit, secondary active indicator 36 is turned off, and primary active indicator 26 is turned on. Wheelchair controller 9 returns to the execution of the operation specified by the original primary command.

A STOP command may be issued at any time. It causes stop indicator 49 to be lit, and all other indicators to be turned off. The wheelchair drive motors are deactivated and all other controls are initialized so that a new primary command may be accepted.

The operations caused by a BRAKE command are similar to those responsive to a STOP command except that BRAKE indicator 33 is also caused to be lit, and if the wheelchair is equipped with brakes, they are activated.

An ERASE command may be issued immediately following a function command which has not yet been activated. It causes the indicator which was caused to be lit by the function command to be turned off and the control system to return to the state it was in before the issuance of the function command.

FIG. 6 is a state diagram illustrating all valid sequences of wheelchair commands. The ovals of FIG. 6 indicate stable states of the control apparatus. The apparatus continues to perform the functions specified within the ovals until a subsequent command causes one of the paths out of the ovals to be taken. The rectangles of FIG. 6 indicate unstable states of the apparatus. The apparatus remains in the states defined by the rectangles only until the specified function(s) are performed. Upon completion of performance the appropriate oval defining a stable state is entered via the paths shown.

FIG. 6 may be best understood by way of example. IDLE mode is indicated by oval 300 and corresponds to the state of the apparatus in which the wheelchair is at rest and the apparatus is ready to accept a first command. Starting in IDLE mode it will be seen that any wheelchair command may be issued. The commands STOP or BRAKE are indicated by line 301. The commands FORWARD or REVERSE are indicated by line 302. The commands LEFT or RIGHT are indicated by line 303. Finally, the commands FASTER or SLOWER are indicated by line 304. Assuming that either a FORWARD or a REVERSE command is issued, oval 305 is reached, wherein the appropriate primary command indicator of display panel 7 is lit. Three paths may be taken out of circle 305. If the next command is ERASE, STOP, or BRAKE, the apparatus returns to IDLE mode oval 300 via line 306. If the next command is GO, rectangle 308 is entered via line 309, and the appropriate ones of control lines 8 to the wheelchair controller are activated to cause the wheelchair to be propelled in the appropriate forward or reverse direction. After activating these control lines, oval 311 is entered via line 310. Referring again to circle 305, if the next command is JOG, rectangle 312 is entered via line 313. As indicated by rectangle 312, the JOG command causes the appropriate ones of control lines 8 to the wheelchair controller to be activated for the jog duration. When the control lines 8 are deactivated, oval 305 is reentered via line 314. Since there are no lines out of oval 305 indicating a LEFT or RIGHT command, these commands are invalid if issued while the apparatus is in the state indicated by oval 305. Similarly, the only commands which may be validly issued when the apparatus is in any of the states indicated by the ovals of FIG. 6, are indicated by the lines leaving those ovals labeled with the appropriate valid commands.

Figure 4:
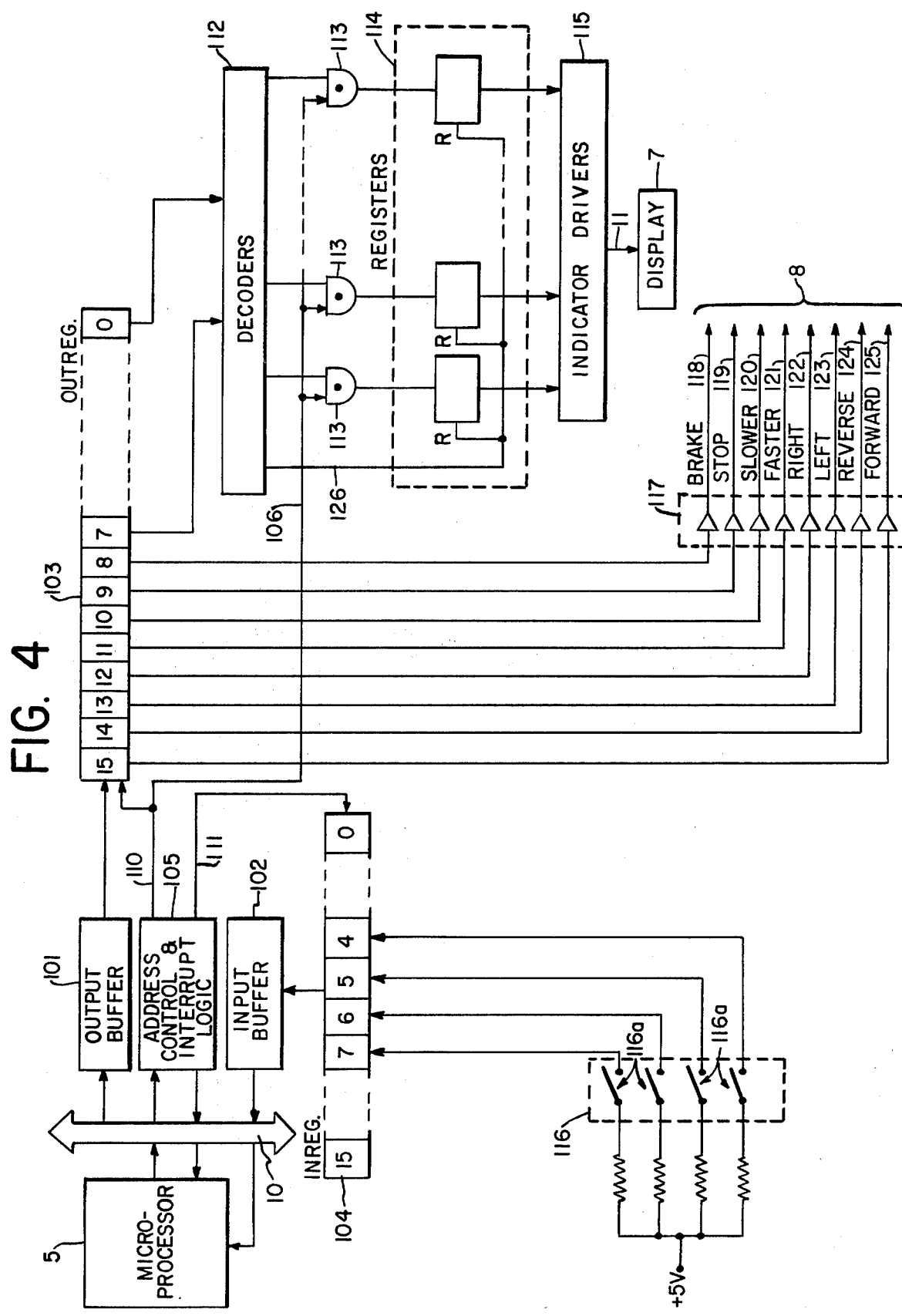
FIG. 4 is a more detailed block diagram of a portion of the apparatus.

Referring to FIG. 4, there is shown in further detail the circuitry included in interface 6 of FIG. 2. Interface 6 includes an output buffer 101 which receives data from microprocessor 5 via system bus 10. Output buffer 101 is connected to a 16 position register 103 which is labeled OUTREG. The output of each one of positions 8 through 15 of OUTREG 103 is connected to one of power drivers 117 for producing an electrical signal on the appropriate one of control lines 8 capable of driving the solenoids of the relay logic of wheelchair controller 9 of FIG. 2. The data in positions 8 through 15 of OUTREG 103 is bit significant: that is, a logical "1" in any one of the positions activates a corresponding one control lines 8 to the wheelchair controller as shown in FIG. 2. Thus, a logical "1" in OUTREG position 8 activates BRAKE control line 118; a logical "1" in position 9 activates STOP control line 119; a logical "1" in position 10 activates SLOWER control line 120; a logical "1" in position 11 activates FASTER control line 121; a logical "1" in position 12 activates RIGHT control line 122; a logical "1" in position 13 activates LEFT control line 123; a logical "1" in position 14 activates REVERSE control line 124; and a logical "1" in position 15 activates line 125.

Control logic unit 105 contains electronic control logic for controlling the flow of data through interface 6. Control logic unit 105 communicates with microprocessor 5 through system bus 10. It controls the flow of data into and out of the OUTREG 103 by means of a plurality of electrical control lines 110, and it controls the flow of data into and out of INREG 104 by means of a plurality of electrical control lines 111; INREG 104 being another 16 position register. One of lines 110 is new data ready line 106 which indicates that there is new data in OUTREG 103. In the present embodiment the lighting of the indicators of display panel 7 is controlled in the following manner. Encoded data signifying the indicators to be lit is set into output buffer 101 by microprocessor 5, and then is set into positions 0 through 7 of OUTREG 103 under the control of control logic unit 105. The data is decoded by decoder 112 to actuate the appropriate data input lines of gates 113. When new data ready line 106 is activated by control logic unit 105, gates 113 are activated to set the data into the appropriate positions of registers 114. If the encoded data is that of a STOP or BRAKE command, reset line 126 is activated by decoders 112 and registers 114 are reset so that all of the indicators of display panel 7 will be turned off except for wheelchair mode indicator 25 and either STOP indicator 49 or the BRAKE indicator 33 of FIG. 3. The outputs of registers 114 are amplified by indicator drivers 115 to provide the required driving voltage to the above selected indicators over indicator drive lines 11.

Each one of the outputs of OUTREG 103 is connected to a corresponding one of power drivers 117, which drive control lines 8 with sufficient power to activate the solenoids of wheelchair controller 9. FIG. 4 illustrates the relation between the particular control lines 118 through 125 and the corresponding bit positions of OUTREG 103. The sequence in which microprocessor 5 causes bits 8 through 15 to be set will be discussed in the portion of this specification relating to the program included in microprocessor 5.

Interface 6 also includes JOG duration switch 116 which, in the present embodiment, is a ten position thumbwheel switch. JOG duration switch 116 includes four switch contacts 116a which are selected for closing according to the position of the thumbwheel. The selective closing of switch contacts 116 causes a code representing the jog duration constant (N) to be set into positions 4 through 7 of INREG 104. The JOG duration constant ranges from the member 1 for thumbwheel position 0 to the number 10 for thumbwheel position 9. Under the control of control logic unit 105, the data in INREG 104 may be set into an input buffer 102 from which it is eventually presented to microprocessor 5 via system bus 10. The method by which microprocessor 5 uses the JOG duration constant to control the JOG duration time will be discussed in the specification relating to the program included in microprocessor 5.

FIGS. 5, 5A and 5B comprise a simplified flow diagram of the program included in microprocessor 5 which controls the lighting of the indicators on display panel 7, and the sequence of activation of control lines 118 through 125 of FIG. 4.

Starting at entry block 201, wheelchair mode block 202 is entered. For the purpose of this description, wheelchair mode is the only valid mode; however, it will be appreciated that other modes 202a, b, etc. such as enviornmental control unit mode or tape recorder mode may be available in other embodiments, which still remain within the spirit and scope of the invention.

In block 203 the program receives the command which has been spoken by the wheelchair's operator and converted to a digital format by voice processor 1 of FIG. 2. Diamond 204 is a decision element wherein a decision is made as to whether the command as issued was valid. This decision is a two-step process. First, the command as issued must be one of a previously determined set of valid commands for the wheelchair mode of operation. In the present embodiment this step is performed by a commercially available program operating in combination with microprocessor 5 of FIG. 2. Second, the command must have been issued in a valid sequence. The state diagram of FIG. 6 may be used to determine the currently allowable commands, given the previous sequence of commands. This state diagram may be converted to program for operation in combination with microprocessor 5 of FIG. 2 to perform the above-mentioned second step by any one of a number of methods known in the art. For example, a table may be constructed in the memory of microprocessor 5 which lists the valid command possible given each possible previous command sequence. The program would keep a command history for use in indexing the table each time a new command was issued to determine the validity of the new command.

Returning to diamond 204 of FIG. 5 if the command issued was invalid, block 205 is entered. The command is ignored and a a binary code corresponding to reject indicator 24 of display panel 7 is set into positions 0 through 7 of OUTREG 103. Upon the activation of new data ready line 106 reject indicator 24 is lit as previously discussed. The program then returns to wheelchair mode block 202 and awaits the next command.

If the decision made in diamond 204 is that the command is valid, diamond 207 is entered. If the command in question is a function command, the "yes" branch out of diamond 207 is taken and diamond 208 is entered. If at the time the command in question is recognized a previously issued primary command is active, that is to say, the primary active indicator 26 of display panel 7 is on and the wheelchair controller is in the process of executing the primary function, the "yes" branch out of diamond 208 is taken and a program indication is set specifying that a secondary command is pending. If, however, a primary command is not currently active, the "no" branch out of diamond 208 is taken and a different program indication is set specifying that a primary command is pending. In either case, block 211 is entered and the appropriate command code is set into positions 0 through 7 of OUTREG 103 for lighting the appropriate indicator of display panel 7 after the activation of new data ready line 106 as shown in block 206. This command code is modified depending on whether the pending command is a primary or a secondary one, so that the command will be displayed by lighting the appropriate indicator in either the primary command column or the secondary command column of the display panel. When the display of the command has been accomplished the program returns to wheelchair mode block 202 to await reception of the next command.

Returning to diamond 207, if the command in question is not a function command (e.g., it is an activation command), the "no" branch out of block 207 is taken and diamond 212 is entered. If the command is a STOP or a BRAKE the "yes" branch out of diamond 212 is taken and diamond 213 is entered. For the sake of simplicity, block 213 indicates that two actions take place simultaneously although in actual practice these actions would be performed sequentially. The first action is to set the command code for the STOP or BRAKE into positions 0 through 7 of OUTREG 103 for lighting the appropriate indicator of display panel 7 by the method specified in blocks 211 and 206. The second action is to enter diamond 214 where a decision is made as to whether a FORWARD command is presently active. If a FORWARD command is active, positions 12 and 15 of OUTREG 103 are set to logical "ones". As illustrated in FIG. 4, the setting of logical "ones" into these positions activates RIGHT control line 122 and FORWARD control line 125 to the wheelchair controller. If a FORWARD command is not currently active, the "no" branch out of diamond 214 is taken, and diamond 216 is entered. If a REVERSE command is currently active, the "yes" branch of diamond 216 is taken and block 217 is entered wherein logical "ones" are set into positions 13 and 14 of OUTREG 103. As illustrated by FIG. 4, the setting of "ones" into these bit positions activates LEFT control line 123 and REVERSE control line 124 to the wheelchair controller. If a REVERSE command is not currently active, the "no" branch of diamond 216 is taken and diamond 218 is entered. If the command in question is a STOP, the "yes" branch of diamond 218 is taken and position 9 of OUTREG 103 is set to a logical "one" as specified by block 219. In all of the three aforementioned cases the next block to be entered is block 221 in which any active indicator of display panel 7 which is currently lit is turned off. After a wait of approximately 250 milliseconds, as indicated by diamond 222, all of positions 8 through 15 of OUTREG 103 are reset to logical "zeros" as indicated by block 223. The program then returns to wheelchair mode block 202 to await the next command.

Returning to diamond 218, if the command in question was not a STOP it must have been a BRAKE and block 220 is entered wherein logical "ones" are set into positions 8 and 9 of OUTREG 103. As illustrated by FIG. 4, the setting of logical "ones" into these positions activates BRAKE control line 118 and STOP control line 119 to the wheelchair controller. The program then proceeds to block 224 where all currently lit active indicators of display panel 7 are turned off. After a wait of approximately 250 milliseconds as indicated by diamond 225, positions 8 through 15 of OUTREG 103 are reset to logical "zeros" except for position 8 which is set to a logical "one", thus leaving BRAKE control line 118 of FIG. 4 in an activated state. The program then returns to wheelchair mode block 202 to await the next command.

Returning to diamond 212, if the command in question was not a STOP or a BRAKE, the "no" branch is taken out of block 212. At this time one of three program paths may be taken depending on the previously set program indications of the pending or active status of the preceding function command. If a previous primary function command is pending and a secondary function command is not pending, block 227 is entered and the program proceeds to diamond 230. If the current command is an ERASE, the "yes" branch of diamond 230 is taken and block 231 is entered wherein the primary pending program indication is reset. If the current command is not an ERASE the "no" branch of diamond 230 is taken and block 232 is entered wherein the primary active indicator 26 of the display panel 7 is lit. The program then proceeds to diamond 238. If the preceding function command was a FORWARD or a REVERSE the "yes" branch of diamond 238 is taken and block 239 is entered. In block 239 the appropriate positions of OUTREG 103 are set to logical "ones", i.e., positions 12 and 15 are set to logical "ones" for a FORWARD command or bits 13 and 14 are set to logical "ones" for a REVERSE command. The setting of these OUTREG positions to "ones" causes the appropriate one of control lines 118 through 125 of FIG. 4 to be activated as previously discussed. After a wait of approximately 250 milliseconds, as indicated by diamond 240, positions 8 through 15 of OUTREG 103 are all reset to logical "zeros" as indicated by block 241, and diamond 242 is entered. If the current activation command is a JOG the "yes" branch of diamond 242 is taken and block 243 is entered. In block 243 the program reads the coded JOG duration constant (N) which had previously been set into positions 4 through 7 of the INREG 104 by JOG duration switch 116 of FIG. 4. The program then waits for time of approximately 200 milliseconds times the value of N, as indicated by diamond 244, before entering block 245. In block 245 the appropriate positions of OUTREG 103 are again set to logical "ones". These positions remain set to logical "ones" for a time of approximately 200 milliseconds, as indicated by diamond 246, before being again reset to logical "zeros" as indicated by block 247. At the time that OUTREG 103 is reset the primary active indicator 26 is also reset, and the primary pending program indication is set. Thus, if the next command is a JOG or a GO the appropriate FORWARD or REVERSE function will again be activated. From block 247 the program proceeds to block 257 to await the issuance of the next command.

Returning to diamond 242, if the current is a GO rather than a JOG, the "no" branch of diamond 242 is taken and the program proceeds directly to block 257. In this case the wheelchair would continue to be propelled in the appropriate FORWARD or REVERSE direction, and the primary active indicator 25 would remain lit while the program awaited the issuance of the next command.

Returning to diamond 238, if the proceeding function command was not a FORWARD or a REVERSE, the "no" branch is taken and diamond 248 is entered. In diamond 248 the previously set active indicators are examined to determine whether the current command is a primary or a secondary one. If the current command is secondary the "yes" branch out of diamond 248 is taken and the positions of OUTREG 103 which had previously been set to logical "ones" by the preceding primary command sequence are caused to maintain their logical "one" setting before the program enters block 250. Block 250 is then entered. If the current command is a primary one, the "no" branch of diamond 248 is taken and block 250 is entered directly.

In block 250 the appropriate position of OUTREG 103 is set to a logical "one" in accordance with the wheelchair function specified by the immediately preceding function command. Thus position 13 is set to a logical "one" for a LEFT function, position 12 is set to a logical "one" for a RIGHT function, position 11 is set to a logical "one" for a FASTER function, and position 10 is set to a logical "one" for a SLOWER function.

If the current activation command is a GO, the "no" branch of diamond 251 is then taken and block 257 is entered directly. If the current activation command is, however, a JOG, the "yes" branch out of diamond 251 is taken and block 252 is entered. In block 252 the program reads the JOG duration constant (N) from positions 4 through 7 of INREG 104 and then waits for a period of approximately 200 milliseconds times N as indicated by diamond 253, before proceeding to block 254. In block 254 the positions of OUTREG 103 which had been set to logical "ones" in block 250 are reset to logical "zeros". The program then proceeds to diamond 255 where, if the current command sequence is a primary one, the "no" branch is taken and the program proceeds to block 256a where primary indicator 26 is turned off and the "primary pending" program indication is set. It will be noted that at this time the appropriate primary function indication of display panel 7 remains lit and that upon reception of another activation command primary function will again be activated. From block 256a the program proceeds to block 257 to await the issuance of the next command.

Returning to diamond 255, if the current command sequence is a secondary one the yes branch is taken and block 256 is entered. In block 256 secondary active indicator 36 is turned off and primary active indicator 26 is lit. Since, as previously discussed, the appropriate ones of control lines 118 through 125 which had originally been activated in response to the primary command sequence had remained activated during the performance of the secondary operation, wheelchair controller 9 now proceeds to propel the wheelchair in the manner specified by the primary function command. While this performance continues the program proceeds to block 257 to await the issuance of the next command.

Returning to the "no" branch of diamond 212, block 228 is entered if a primary command sequence is currently active and a secondary function is pending. If the current command is an ERASE the "yes" branch of diamond 233 is taken and the secondary pending program indication is reset while the execution of the primary function continues. The program then goes to block 257 to await the issuance of the next command. If the current command is not an ERASE, block 234 is entered wherein primary active indicator 26 is turned off, the primary pending program indication is set, and secondary active indicator 36 is lit. The program then goes to diamond 238 for execution of the secondary function as previously discussed.

Returning again to the "no" branch of diamond 212, if a secondary function is currently active and a primary function is pending, block 229 is entered. The only valid command in this state of the apparatus is a CANCEL as indicated by block 236. The program proceeds to block 237 where secondary active indicator 36 is turned off and primary active indicator is lit. Since, as previously discussed, the ones of control lines 118 through 125 which had originally been activated as a result of the primary command sequence remained activated during the execution of the secondary function, wheelchair controller 9 now proceeds to propel the wheelchair in the manner specified by the primary function command. The program proceeds to block 257 to await the issuance of the next command.

To summarize, microprocessor 5 in accordance with the program of FIGS. 5A, 5B and 5C first determines the validity of any command issued by the operator so as to prevent the execution of any sequences of wheelchair operation which could prove to be dangerous. Upon the issuance of the function command of a command sequence, microprocessor 5 causes the illumination of the appropriate indicators of display panel 7 so as to inform the operator of the function which is about to be performed. If the operator wishes the indicated function to be performed, he issues an activation command which activates microprocessor 5 to cause the appopriate ones of control lines 8 to the wheelchair controller 9 to be activated. If the activation command is a GO, control lines 8 are activated such that wheelchair controller 9 is caused to propel the wheelchair in the specified manner until the operation is terminated by a subsequent command issued by the operator. If, however, the activation command is a JOG, control lines 8 are activated such that the wheelchair controller is activated only for a preselected time period, after which time the operation terminates automatically.

FIG. 7 is a circuit diagram of the wheelchair controller 9 of FIG. 2. While in the present embodiment the wheelchair controls are formed mainly of mechanical relays, it will be appreciated by one skilled in the art that the same functions could be performed by transistors or other suitable electronic components.

The operation of the wheelchair controller may be best understood by way of operational examples describing the sequence of operations carried out by the controller responsive to the activation or deactivation of control lines 118 through 125. It will be recalled that the activation and deactivation of these control lines is controlled by microprocessor 5, in combination with the program included therein, responsive to the command sequences spoken by the wheelchair operator. It will also be recalled, that the functional commands of RIGHT, LEFT, FORWARD, REVERSE, FASTER and SLOWER require the issuance of a subsequent activation command of JOG or GO before the appropriate control lines are activated. For the sake of simplicity, the first part of the discussion below will assume that the command sequences are of the primary type.

FORWARD-GO

For the command sequence of FORWARD-GO it will be recalled that RIGHT control line 122 and FORWARD control line 125 are activated for a period of approximately 250 milliseconds and then deactivated. The activation of these control lines causes current to flow through relay coils 304 and 308 to ground thereby causing the normally open contact 303 of relay 301 and the normally open contact 307 of relay 305 to be selected. Upon the selection of these two relay contacts current flows from the +24 volt terminal of relay 301 through normally open contact 303, normally open contact 307, diode 317 and coil 319 of alternating latch 320 to ground. In the preferred embodiment alternating latch 320 is a conventional component which has the characteristic that if the normally open contact 324 of the latch is in its normal unselected state the initiation of current flow through coil 319 causes normally open point 324 to be selected and remain selected even after the current flow through coil 319 is terminated. Normally open contact 324 would again be caused to be deselected by a subsequent application of current through coil 319. For the purpose of the present discussion it will be assumed that emergency stop switch 326 remains open.

The selection of normally open contacts 303 of relay 301 and 307 of relay 305 also allows current to flow through diode 392, diode 336 and relay coil 338 to ground. Current also flows through diode 392, diode 359 and relay coil 358 to ground. This flow of current through relay coils 338 and 358 causes the selection of normally open contact 332 of relay 330, normally open contact 335 of relay 333, normally open contact 354 of relay 352 and normally open contact 357 of relay 355. With these contacts selected, current is allowed to flow from the +24 volt terminal of right motor speed control 389, through the right motor speed control 389, normally closed contact 362 of relay 361, right wheel drive motor 370, normally open contact 332 of relay 330 and thence back to the −24 volt terminal of right motor speed control 389. Current is also allowed to flow from the +24 volt terminal of right motor speed control 389, through right motor speed control 389, normally closed contact 340 of relay 339, left wheel drive motor 371, normally open contact 354 of relay 352 and thence back to the −24 volt terminal of left motor speed control 391. It will be noted that the direction of current flow through both left wheel drive motor 371 and right wheel drive motor 370 is in a bottom-to-top direction on the diagram. This direction of current flow causes the drive motors 370 and 371 to turn their respective wheels in a forward direction.

As noted previously in the discussion of FIG. 5, RIGHT control line 122 and FORWARD control line 125 remain activated for a period of approximately 250 milliseconds and are then deactivated. The deactivation of these control lines terminates the flow of current through relay coils 304 and 308 which allows normally open contact 303 of relay 301 and normally open contact 307 of relay 305 to return to their deselected states. Normally open contact 324 of alternating latch 319 remains selected, however, until the next application of current through coil 319. Current therefore continues to flow through normally open contact 324 to energize relay coils 338 and 358. Consequently, current continues to flow through the right wheel drive motor 370 and the left wheel drive motor 371 and the wheelchair continues to be driven in a forward direction.

REVERSE-GO

In response to the command sequence of REVERSE-GO, LEFT control line 123 and REVERSE control line 124 are caused to be activated for approximately 250 milliseconds as explained previously in the discussion of FIG. 5. The activation of the LEFT control line 123 causes current to flow through relay coil 312 to ground and the activation of the REVERSE control line 125 causes current to flow through relay coil 316 to ground. The flow of current through these relay coils causes normally open contact 311 of relay 309 and normally open contact 315 of relay 313 to be selected. With these relay contacts selected, current flows from the +24 volt terminal of relay 309 through normally open contact 311, normally open contact 315 of relay 313, diode 318, and coil 319 to ground, thereby causing normally open contact 324 of alternating latch 320 to be selected. Current also flows through diode 327, diode 346, and relay coil 347 to ground, and through diode 327, diode 368, and relay coil 367 to ground. The flow of current through relay coils 347 and 367 causes the selection of normally open contact 341 of relay 339, normally open contact 344 of relay 342, normally open contact 363 of relay 361, and normally open contact 366 of relay 364. With these relay contacts selected current is allowed to flow from the +24 volt terminal of right motor speed control 389, through the right motor speed control 389, normally closed contact 331 of relay 330, right wheel drive motor 370, normally open contact 363 of relay 361 and thence back to the −24 volt terminal of right motor speed control 388. Current also flows from the +24 volt terminal of left motor speed control 391, through the left motor speed control 391, normally closed contact 353 of relay 352, left wheel drive motor 371, normally open contact 341 of relay 339 and thence back to the −24 volt terminal of right motor speed control 389. It will be noted that the current flow through left wheel drive motor 371 and right wheel drive motor 370, in this case is in a top-to-bottom direction on the diagram. This direction of current flow causes the drive motors to turn their respective wheels in a reverse direction.

LEFT control line 123 and REVERSE control line 124 remain activated for a period of approximately 250 milliseconds, and are then deactivated. Since normally open contact 324 of alternating latch 320 remains selected after the deactivation of LEFT control line 123 and REVERSE control line 124, current continues to flow through relay coils 347 and 367, and the appropriate relay contacts for REVERSE operation of the wheelchair remain selected after the deactivation of these control lines.

RIGHT-GO

When a command sequence of RIGHT-GO is spoken by the wheelchair operator, RIGHT control line 122 is activated as previously explained in the discussion of FIG. 5. RIGHT control line 122 remains activated until a STOP or BRAKE command is issued. The activation of RIGHT control line 122 causes current to flow through relay coil 304 to ground which in turn causes normally open contact 303 of relay 301 to be selected. With normally open contact 303 selected current flows from the +24 volt terminal of relay 301, through normally open contact 303, normally closed contact 306 of relay 305, diode 350 and relay coil 358 to ground. Current also flows through diode 351 and relay coil 367 to ground. The flow of current through relay coils 358 and 367 causes the selection of normally open contact 354 of relay 352, normally open contact 357 of relay 355, normally open contact 363 of relay 361, and normally open contact 366 of relay 364. With these relay contacts selected, current flows from the +24 volt terminal of right motor speed control 389 through right motor speed control 389, normally closed contact 340 of relay 339, left wheel drive motor 371, normally open contact 354 of relay 352 and thence back to the −24 volt terminal of left motor speed control 391. Current also flows from the +24 volt terminal of right motor speed control 389 through right motor speed control 389, normally closed contact 331 of relay 330, right wheel drive motor 370, normally open contact 363 of relay 361, and thence back to the −24 volt terminal of right motor speed control 389. It will be noted that in this case current flows through the right wheel drive motor 370 in a top-to-bottom direction on the diagram and current flows through the left wheel drive motor 371 in a bottom-to-top direction in the diagram. Consequently, the left wheel of the wheelchair is driven in a forward direction, and the right wheel of the wheelchair is driven in a reverse direction, thus causing the wheelchair to turn in a left-to-right or clockwise direction.

LEFT-GO

The issuance of the command sequence LEFT-GO by the wheelchair's operator causes the LEFT control line 123 to be activated as previously explained in the discussion of FIG. 5. The activation of LEFT control line 123 causes current to flow through relay coil 312 to ground which consequently causes normally open contact 311 of relay 309 to be selected. With normally open contact 311 selected, current flows from the +24 volt terminal of relay 309, through normally open contact 311, normally closed contact 314 of relay 313, diode 328 and relay coil 347 to ground. Current also flows through diode 329 and relay coil 338 to ground. The flow of current through relay coils 338 and 347 causes the selection of normally open contact 332 of relay 330, normally open contact 335 of relay 333, normally open contact 341 of relay 339 and normally open contact 344 of relay 342. With these relay contacts selected, current flows from the +24 volt terminal of right motor speed control 389, through right motor speed control 389, normally closed contact 362 of relay 361, right wheel drive motor 370, normally open contact 332 of relay 330 and thence back to the −24 volt terminal of right motor speed control 389. Current also flows from the +24 volt terminal of left motor speed control 391, through left motor speed control 391, normally open contact 353 of relay 352, left wheel drive motor 371, normally open contact 341 of relay 339 and thence back to the −24 volt terminal of right motor speed control 389. It will be noted that in this case current flows through left wheel drive motor 371 in a top-to-bottom direction on the diagram and current flows through right wheel drive motor 370 in a bottom-to-top direction on the diagram. The right wheel of the wheelchair is consequently driven in a forward direction, and the left wheel of the wheelchair in a reverse direction, thus causing the wheelchair to turn in a right-to-left or counterclockwise direction.

FASTER-GO

The issuance of the command sequence FASTER-GO by the wheelchair's operator causes the activation of FASTER control line 121 as explained in the discussion of FIG. 5. The activation of FASTER control line 121 causes current to flow through relay coil 379 to ground thereby causing normally open contact 378 of relay 376 and normally open contact 375 of relay 373 to be selected. With these relay points selected, current flows from the positive terminal of battery 372, through normally open contact 378 of relay 376, speed control motor 387, normally open contact 375 of relay 373 and thence back to the negative terminal of battery 372. The resulting flow of current through speed control motor 387 causes the motor to move the taps of potentiometers 388 and 390 in a direction which increases the amount of possible current flow through left motor speed control 391 and right motor speed control 389. Right wheel drive motor 370 and left wheel drive motor 371 will thereby turn at a faster rate when activated by a FORWARD, REVERSE, LEFT, OR RIGHT command sequence.

SLOWER-GO

In response to a command sequence of SLOWER-GO, SLOWER control line 120 is activated as previously explained. The activation of SLOWER control line 120 causes current to flow through relay coil 386 to ground thereby causing normally open contact 385 of relay 383 and normally open contact 382 of relay 380 to pick. With these relay contact selected, current flows from the positive terminal of battery 372, through normally closed contact 377 of relay 376, normally open contact 385 of relay 383, speed control motor 387, normally open contact 382 of relay 380, normally closed contact 374 of relay 373, and thence back to the negative terminal of battery 372. It will be noted that the resulting current flow through speed control motor 387 is in a left-to-right direction on the diagram, which is the reverse of the current flow produced by the command sequence of FASTER-GO. The left-to-right flow of current through speed control motor 387 causes the motor to move the taps of potentiometers 388 and 390 in a direction which decreases the possible current flow through right motor speed control 389 and left motor speed control 390. Right wheel drive motor 370 and left wheel drive motor 371 will thereby turn at a slower rate when activated by a FORWARD, REVERSE, RIGHT, or LEFT command sequence.

The following discussion describes the operations which take place in wheelchair controller when the activation command of a command sequence is a JOG rather than a GO.

FORWARD-JOG, REVERSE-JOG

The command sequence of FORWARD-JOG, or REVERSE-JOG causes the activation for approximately 250 milliseconds of the appropriate control lines 125, 122, 124 and 123 for initiating the desired FORWARD or REVERSE movement of the wheelchair as discussed previously. As also discussed previously, the appropriate relay contact for maintaining the desired FORWARD or REVERSE movement of the wheelchair remain selected because of the current flow through normally open contact 324 of alternating latch 320, which remains in its picked position after the deactivation of the control lines.

In the case of the FORWARD-JOG command sequence, microprocessor 5 causes a second 250 nanosecond activation of RIGHT control line 122 and FORWARD control line 125 after waiting for a JOG duration time the length of which is controlled by the position to which JOG duration switch 116 is set, as previously discussed. The activation of these control lines causes current to again flow through diode 317 and coil 319 to ground. Since at this time normally open contact 324 of alternating latch 320 is selected, the flow of current through coil 319 causes normally open contact 324 to return to its open position. The opening of normally open contact 324 terminates the flow of current through relay coils 338 and 358. The deactivation of these coils allows normally open contact 335 of relay 333, normally open contact 332 of relay 330, normally open contact 357 of relay 355, and normally open contact 354 of relay 352 to be deselected. The deselection of these relay contacts terminates the flow of current through right wheel drive motor 370 and left wheel drive motor 371 thereby causing the wheelchair to stop.

In the case of the command sequence REVERSE-JOG, the program means causes a second 250 millisecond activation of REVERSE control line 124 and LEFT control line 123, after waiting for the JOG duration period. Activation of these control lines causes current to flow through diode 31 and coil 319 to ground which, in the manner above-described for the FORWARD-JOG sequence deselects normally open contact 324 of alternating latch 320, thereby stopping the wheelchair.

LEFT-JOG, RIGHT-JOG, SLOWER-JOG, FASTER-JOG

In the above-described GO initiated command sequences for the function commands of LEFT, RIGHT, FASTER, and SLOWER, microprocessor 5 left the appropriate one of control lines 123, 122, 120 or 121 in its activated state, rather than deactivating it after 250 milliseconds as in the case of the FORWARD-GO or REVERSE-GO command sequences. It will be noted that coil 319 of alternating latch 320 is never activated by a LEFT, RIGHT, FASTER or SLOWER command sequence. The deactivation of these control lines, therefore, causes the appropriate relay contacts which had been selected in response to the activation of the control lines to again be deselected, thereby causing the operation to terminate. In response to any of the above JOG initiated control sequences, microprocessor 5, therefore, first causes the activation of the appropriate one of control lines 123, 122, 120 or 121 and then, after waiting for the appropriate JOG duration period, deactivates the control line. The operation thus proceeds for a period of time equal to the JOG duration period.

The previous discussions dealt with command sequences of the primary type. It is a feature of the present invention that secondary command sequences are provided for which allow the wheelchair's operator to modify the speed or direction of travel of the chair without the need to first stop the chair. Coupled with the above-described JOG facility, this secondary command facility allows the wheelchair's operator to make small, incremental direction changes which are useful in correcting any "drift" of the chair which may be caused by travel over slightly irregular terrain.

A secondary command sequence is initiated by the issuance by the wheelchair's operator of a second command sequence while a primary command sequence is active and in the process of being executed by the wheelchair controller. It will be appreciated by reference to the state diagram of FIG. 6 that the FORWARD and REVERSE commands are valid only as a part of a primary command sequence. It will be further appreciated by reference to FIG. 6 that the LEFT, RIGHT, FASTER, or SLOWER commands which are otherwise valid as part of a secondary command sequence may nevertheless be invalid if they are issued while certain primary command sequences are active. For example, the directional command LEFT is invalid as part of a secondary command sequence if the primary command sequence included a RIGHT command.

The following discussion describes the operations performed by the wheelchair controller in response to the issuance of a valid secondary command sequence, after a given primary command sequence.

PRIMARY FORWARD-GO, SECONDARY RIGHT-GO

As noted previously, a primary FORWARD-GO command sequence causes a 250 millisecond activation of RIGHT control line 122 and FORWARD control line 124 which leaves normally open contact 324 of alternating latch 320, normally open contact 337 of relay 333, normally open contact 332 of relay 330, normally open contact 357 of relay 355, and normally open contact 354 of relay 352 selected, all other relay contacts being in their normal states. Given this state of the relays, drive motors 370 and 371 are activated to propel the chair in a FORWARD direction. In response to a secondary command sequence of RIGHT-GO, microprocessor 5 causes RIGHT control line 122 to become and remain activated. The activation of RIGHT control line 122 allows current to flow through relay coil 304 to ground which in turn causes normally open contact 303 of relay 301 to be selected. With normally open contact 303 selected, current flows from the +24 volt terminal of relay 301 through normally open contact 303, normally closed contact 306 of relay 305, diode 351 and relay coil 367 to ground. The flow of current through relay coil 367 causes normally open contact 366 of relay 364 and normally open contact 363 of relay 361 to be selected. (It will be noted that a current path is also provided through diode 350 and relay coil 358 to ground. This current path, however, has no effect since, as previously noted, relay coil 358 is already energized at this time through the path of normally open contact 324 of alternating latch 320, normally open contact 355 of relay 333, normally open contact 357 of relay 355, diode 349, and diode 359.) With the appropriate relay contacts selected as above-described, current is allowed to flow from the +24 volt terminal of right motor speed control 389 through right motor speed control 389, normally closed contact 340 of relay 339, LEFT wheel drive motor 371, normally open point 354 of relay 352, and thence back to the −24 volt terminal of left motor speed control 391. It will be noted, however, that because of the selection of normally open contact 363 of relay 361, the pre-existing current path to right wheel drive motor 370 is broken, and the right wheel of the wheelchair therefore stops turning. Since the flow of current through left wheel drive motor 371 is in a bottom-to-top direction on the diagram, the LEFT wheel of the wheelchair is driven in a forward direction and the wheelchair thus turns in a left-to-right or clockwise direction.

PRIMARY FORWARD-GO, SECONDARY LEFT-GO

For the same reasons as described in the above discussion of the secondary RIGHT-GO sequence, a primary command sequence of FORWARD-GO will leave relay coils 338 and 358 energized and the appropriate normally open relay contacts selected. Issuance of a secondary LEFT-GO sequence of commands by the wheelchair's operator causes LEFT control line 123 to become and remain activated as previously described. The activation of LEFT control line 123 allows current to flow through relay coil 312 to ground thereby causing normally open contact 311 of relay 309 to be selected. With normally open contact 311 selected, current flows from the +24 volt terminal of relay 309, through normally open contact 311, normally closed contact 314 of relay 313, diode 328, and relay coil 347 to ground. The flow of current through relay coil 347 causes the selection of normally open contact 344 of relay 342 and normally open contact 341 of relay 339. With these relay contacts selected, current flows from the +24 volt terminal of right motor speed control 389 through right motor speed control 389, normally closed contact 362 of relay 361, right wheel drive motor 370, normally open contact 332 of relay 330, and thence back to the −24 volt terminal of right motor speed control 389. The current path to left wheel drive motor 371 is broken, however, by the selection of normally open contact 341 of relay 339, and the left wheel of the wheelchair therefore comes to a stop. Since current flows through right wheel drive motor 370 in a bottom-to-top direction on the diagram, the right wheel of the wheelchair continues to turn in a forward direction and the wheelchair is thus caused to move in a right-to-left or counterclockwise direction.

PRIMARY FORWARD-GO, SECONDARY RIGHT-JOG OR LEFT-JOG

If a secondary RIGHT or LEFT command is activated by a JOG command rather than a GO command, the appropriate one of control lines 122 or 123 is activated in the manner described above for the RIGHT-GO and LEFT-GO sequences. In the case of a JOG activated command sequence, however, the appropriate control line is deactivated after the JOG duration period. In the case of the secondary RIGHT-JOG command sequence, the deactivation of RIGHT control line 122 allows normally open contact 363 of relay 361 to again be deselected thereby again allowing current to flow through right wheel drive motor 370 in a bottom-to-top direction. The wheelchair then resumes its forward motion as specified by the primary FORWARD-GO command sequence. Similarly, the deactivation of LEFT control line 123 allows normally open contact 341 of relay 339 to again be deselected thereby allowing current to again flow through left wheel drive motor 371 in a bottom-to-top direction. Again, the wheelchair again resumes its forward motion as specified by the primary FORWARD-GO command sequence.

PRIMARY REVERSE-GO, SECONDARY RIGHT-GO

A primary command sequence of REVERSE-GO causes REVERSE control line 124 and LEFT control line 123 to be activated for a period of 250 milliseconds which in the manner previously described leaves normally open contact 324 of alternating latch 320, normally open contact 341 of relay 339, normally open contact 344 of relay 342, normally open contact 363 of relay 361, and normally open contact 366 of relay 364 selected. A secondary command sequence of RIGHT-GO causes RIGHT control line 122 to become and remain activated in the manner also previously described. The activation of RIGHT control line 122 causes, current to flow through relay coil 304 to ground, thereby causing normally open contact 303 of relay 301 to be selected. Current is consequently allowed to flow from the +24 volt terminal of relay 301, through normally open contact 303, normally closed contact 306 of relay 305, diode 350 and relay coil 358 to ground. The flow of current through relay coil 358 causes normally open contact 357 of relay 355 and normally open contact 354 of relay 352 to be selected. With these relay contacts selected, current continues to flow from the +24 volt terminal of right motor speed control 389 through right motor speed control 389, normally closed contact 331 of relay 330, right wheel drive motor 370, normally open contact 363 of relay 361, and thence back to the −24 volt terminal of right motor speed control 389. The current path through left wheel drive motor 371 is broken, however, by the selection of normally open contact 341 of relay 339. The left wheel of the wheelchair thus comes to a stop while the right wheel of the wheelchair turns in a backward direction. The wheelchair is thereby caused to turn in a left-to-right or clockwise direction.

Primary REVERSE-GO, Secondary LEFT-GO

In a similar manner to that described above for the secondary RIGHT-GO command sequence, a secondary LEFT-GO command sequence causes LEFT control line 123 to be activated which in turn causes normally open contact 354 of relay 352 to be selected thereby terminating the flow of current through left wheel drive motor 370 while allowing current to continue to flow through right wheel drive motor 370 in a top-to-bottom direction. The wheelchair's right wheel is thereby stopped while the wheelchair's left wheel continues to turn in a backward direction thereby causing the wheelchair to turn in a right-to-left or counterclockwise direction.

Primary REVERSE-GO, Secondary RIGHT-JOG or LEFT-JOG

The operation of the wheelchair controller in response to a secondary RIGHT-JOG or LEFT-JOG command sequence following a primary REVERSE-GO sequence is similar to the operations described above for the corresponding GO activated secondary command sequence. In the case of the JOG activated sequences, however, the flow of current through the appropriate left or right wheel drive motor is interrupted only for the JOG duration time. The wheelchair is thus caused to make a small directional change before continuing to proceed in the reverse direction.

STOP or BRAKE Commands

As previously discussed, the STOP and BRAKE commands may be validly issued at any time, and act to terminate the wheelchair operation initiated by any previous primary or secondary command sequence.

If a FORWARD or REVERSE command sequence is active at the time of the issuance of the STOP command, microprocessor 5 causes the appropriate ones of control lines 125, 124, 123 and 122 to be activated for a period of approximately 250 milliseconds. As discussed previously in the portion of this description relating to the FORWARD-JOG and REVERSE-JOG sequences of commands, the activation of these control lines causes normally open contact 324 of alternating latch 320, which had previously been selected, to again be deselected, thereby allowing the appropriate relay contacts necessary for forward or reverse operation to return to be deselected. As a consequence of the deselection of these relay contacts the wheelchair comes to a halt.

If a command sequence other than a FORWARD or REVERSE sequence is active at the time of issuance of the STOP command, STOP control line 119 is activated for a 250 millisecond period and all other control lines are deactivated thereby causing the active operation to terminate.

The BRAKE command operates similarly to the STOP command except that in addition to those actions initiated by the STOP command, BRAKE control line 118 is caused to become and remain activated. In a wheelchair so equipped, BRAKE control line 113 may be used to activate the wheelchair brakes.

It will be noted that the closing of the emergency stop switch 11 by the wheelchair operator will allow current to flow from the +24 volt terminal of that switch, through solenoid 319 to ground. The wheelchair is thus caused to stop in a manner similar to the stopping of the chair by means of the STOP command. If the chair is stopped by means of the emergency switch 11, however, a STOP command should subsequently be issued to set the relays of the wheelchair controller to their normal states.

BREATH CONTROLLED OPERATION

It is a feature of the present embodiment of the wheelchair controller that it is adapted to be alternatively operated by means of the breath tubes 12 of FIG. 1. To accomplish this mode of operation pressure switches 392, 393, 394, 395, 397 and 398 are adapted to close when the operator "puffs" or "sips" upon an appropriate one of breath tubes 12. The closing of each one of these switches causes current to flow through its corresponding solenoid thereby causing the wheelchair controller to initiate the appropriate wheelchair function in the same manner as if the function was voice activated. It is anticipated that this feature will prove useful in situations in which the voice processor 1 of the system becomes inoperable. Such a situation could occur, for example, in a high-noise environment.

A voice activated, powered wheelchair control apparatus has been described which provides the wheelchair's operator with a high degree of flexibility in controlling the movement of the chair while at the same time preventing him from causing the chair to perform operation which could be dangerous. Small positioning movements of the chair may be made while it is at rest or traveling either in a forward or reverse direction. The speed of travel of the chair may be selected while it is at rest or varied either continuously or in small increments while it is in motion.

What is claimed is:

1. A wheelchair-mounted control apparatus for controlling a powered wheelchair comprising:
    a voice processor for converting any of a set of preselected spoken command words into corresponding computer-recognizable signals, said spoken words corresponding to desired operations for said wheelchair;
    a microcomputer operatively connected to said voice processor including an identifier for identifying a particular sequence of said signals, corresponding to a preselected sequence of said spoken commands including a first spoken function command for specifying the function to be performed by said wheelchair and a subsequently spoken activation command for conditioning said specified function to be performed by said wheelchair, as a command sequence and also including a set of control lines and a first activator responsive to the identification of said command sequence for selectively activating said control lines; and
    a wheelchair controller including a left and a right wheel drive motor, for propelling said wheelchair in response to the activation of said control lines.

2. Apparatus in accordance with claim 1 wherein said microcomputer further includes:
    an identifier for producing a primary command signal responsive to a first spoken command sequence;
    an identifier for producing a secondary command signal responsive to a subsequently spoken command sequence;
    an activator responsive to said primary command signal for selectively activating said set of control lines; and
    an activator responsive to said secondary command signal for selectively activating said set of control lines and maintaining said control lines activated in response to said primary command signal.

3. Apparatus in accordance with claim 2 wherein said activation command comprises a JOG command and wherein said microcomputer further includes:
    an activator responsive to said signals corresponding to said JOG command for activating said control lines for a preselected JOG duration time period.

4. Apparatus in accordance with claim 3 further comprising:
    an electrical JOG duration switch, including a plurality of selectively activatable switch terminals operatively connected to said microcomputer; and
    wherein said microcomputer further includes means responsive to the activation of a said selected switch terminal for correspondingly determining the length of said JOG duration time period.

5. Apparatus in accordance with claim 4 wherein said activation command comprises one of a plurality of JOG commands, each of said JOG commands uniquely corresponding to a multiplier constant and wherein said microcomputer further includes:

an activator responsive to said signals corresponding to each one of said JOG commands for activating said control lines for a JOG duration time period which is proportional to the corresponding multiplier constant.

6. Apparatus in accordance with claim 2 wherein said first activator includes:

a control line selector responsive to the identification of said function command for selecting for activation a control line corresponding to said function command;

a control line activator responsive to the identification of said activation command for activating said selected control line.

7. Apparatus in accordance with claim 6 wherein said identifier includes:

means for identifying a FORWARD command for conditioning said wheelchair to be propelled in a forward direction;

means for identifying a REVERSE command for conditioning said wheelchair to be propelled in a reverse direction;

means for identifying a RIGHT command for conditioning said wheelchair to turn in a clockwise direction;

means for identifying a LEFT command for conditioning said wheelchair to turn in a counterclockwise direction;

means for identifying a FASTER command for conditioning the speed of travel of said wheelchair to be increased; and means for identifying a SLOWER command for conditioning the speed of travel of said wheelchair to be decreased.

8. Apparatus in accordance with claim 7 wherein said microcomputer further comprises:

means for storing a code corresponding to said function command of said primary command sequence; and a secondary command inhibitor selectively activated by said stored code for preventing the activation of said control lines responsive to said activation command of said subsequently spoken command sequence if said subsequently spoken command sequence includes one of a preselected subset of said function commands which could condition the wheelchair to operate in a dangerous manner.

9. Apparatus in accordance with claim 8 further comprising:

means responsive to said secondary command signal and to the identification of said FORWARD command or said REVERSE command for activating said secondary command inhibitor.

10. Apparatus in accordance with claim 9 further comprising:

means responsive to said secondary command signal, and to a stored code corresponding to said RIGHT command or said LEFT command, and to the identification of said RIGHT command or said LEFT command, for activating said secondary command inhibitor.

11. Apparatus in accordance with claim 7 wherein said wheelchair controller comprises:

a left and a right speed controller, each including a variable speed controller for producing a speed control signal, for limiting the maximum current which may flow through the corresponding one of said drive motors to a valve proportional to the amplitude of said speed control signals; and a speed control motor operatively connected to said variable speed controllers for causing the amplitude of said speed control signals to be increased or decreased;

said speed control motor acting in response to the activation of said control line corresponding to said FASTER command to cause the amplitude of said speed control signals to be increased, and acting in response to the activation of said control line corresponding to said SLOWER command to cause the amplitude of said speed control signal to be decreased.

12. Apparatus in accordance with claim 11 wherein said speed control motor acts responsive to the activation of said control lines corresponding to said FASTER command or said SLOWER command for said JOG duration time period to correspondingly increase or decrease the amplitude of said speed control signals by an amount proportional to the length of said JOG duration time period.

13. Apparatus in accordance with claim 3 wherein said first identifier includes;

means for identifying a RIGHT command for conditioning said wheelchair to turn in a clockwise direction; and means for identifying a LEFT command for conditioning said wheelchair to turn in a counterclockwise direction; and wherein said JOG command activator includes means responsive to the identification of said RIGHT command or said LEFT command for causing said wheelchair controller to correspondingly turn the chair during said time period.

14. Apparatus in accordance with claim 3 wherein said first identifier includes:

means for identifying a FORWARD command for conditioning said wheelchair to be propelled in a forward direction; and means for identifying a REVERSE command for conditioning said wheelchair to be propelled in a reverse direction; and wherein said JOG command activator includes means responsive to the identification of said FORWARD command or said REVERSE command for causing said wheelchair controller to correspondingly propel said wheelchair during said time period.

* * * * *